United States Patent
Ozaki (10) Patent No.: US 6,763,082 B2
(45) Date of Patent: Jul. 13, 2004

(54) X-RAY COMPUTER TOMOGRAPHY APPARATUS

(75) Inventor: Masahiro Ozaki, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/373,048

(22) Filed: Feb. 26, 2003

(65) Prior Publication Data

US 2003/0161435 A1 Aug. 28, 2003

(30) Foreign Application Priority Data

Feb. 27, 2002 (JP) .......................................... 2002-051878

(51) Int. Cl.[7] .............................................. A61B 6/03
(52) U.S. Cl. ............................... 378/8; 378/15; 378/19; 378/901
(58) Field of Search ........................... 378/4, 8, 15, 19, 378/901

(56) References Cited

U.S. PATENT DOCUMENTS

| | | | |
|---|---|---|---|
| 5,231,651 A | | 7/1993 | Ozaki et al. |
| 5,459,769 A | | 10/1995 | Brown |
| 5,594,772 A | * | 1/1997 | Toki et al. .................. 378/114 |
| 5,612,985 A | * | 3/1997 | Toki et al. ..................... 378/4 |
| 2003/0076920 A1 | * | 4/2003 | Shinno et al. ................. 378/4 |

FOREIGN PATENT DOCUMENTS

JP      7-204198      8/1995

* cited by examiner

*Primary Examiner*—David V Bruce
(74) *Attorney, Agent, or Firm*—Oblon, Spivak, McClelland, Maier & Neustadt, P.C.

(57) ABSTRACT

An X-ray computer tomography apparatus of this invention has a function of monitoring, by a pre-scan, a density of a contrast medium in ROI of an object, stopping the pre-scan on the basis of a timing at which the density reaches to a predetermined value, and starting a main-scan. A main-scan condition is initially set based on a physiological phenomenon of the object measured before the injection of the contrast medium. The necessity of resetting an initially set main scan condition is determined on the change of a physiological phenomenon measured before the end of the pre-scan. If it is determined that the main scan condition needs to be reset, the main scan condition is reset from the initially set main scan condition to a main scan condition corresponding to the physiological phenomenon measured before the end of the pre-scan.

20 Claims, 9 Drawing Sheets

FIG. 1

| HEART RATE (HR) | HELICAL PITCH (HP) | SCAN SPEED (SS) |
|---|---|---|
| 40~50 | 0.7 | 1.0 |
| 50~60 | 0.8 | |
| 60~70 | 0.9 | 0.7 |
| 70~80 | 1.0 | |
| 90~100 | 1.1 | |
| 100~110 | 1.2 | 0.4 |
| 110~120 | 1.3 | |

X-RAY COMPUTER TOMOGRAPHY APPARATUS

CROSS-REFERENCE TO RELATED APPLICATIONS

This application is based upon and claims the benefit of priority from the prior Japanese Patent Application No. 2002-051878, filed Feb. 27, 2002, the entire contents of which are incorporated herein by reference.

BACKGROUND OF THE INVENTION

1. Field of the Invention

The present invention relates to an X-ray computer tomography apparatus having a function of executing a pre-scan before a main-scan.

2. Description of the Related Art

In contrast-medium imaging, it is important to start a scan (main-scan) at the timing a contrast medium injected into an object to be examined flows into a region of interest. For this reason, a scan (pre-scan) is executed before a main-scan. In order to suppress the x-ray dosage, a pre-scan is executed by using X-rays lower in intensity than those used in a main-scan. The projection data acquired in a pre-scan is supplied for real-time reconstruction processing. The image (tomographic image) reconstructed in real time is instantly displayed. An imaging technician visually checks the contrast medium concentration (the degree of staining) of a region of interest on the image. Upon determining that the contrast medium concentration of the region of interest has reached a predetermined concentration, the imaging technician presses a trigger button for a main-scan. When the trigger button is pressed, a pre-scan is stopped, and a preparation (setup) for a main-scan is started. The preparation for the main-scan includes the operation of moving the couch into a predetermined scan range, the operation of accelerating the couch to a predetermined speed, the operation of accelerating the rotating frame to a predetermined scan speed, the operation of heating the filament, and the like. Upon completion of the preparation for the main-scan, the main-scan is started.

A technique called bolus tracking method has been developed, in which imaging technician's operation of pressing the trigger button is automated. In bolus tracking method, the CT value or average value of a region of interest is extracted from an image obtained by a pre-scan and compared with a threshold. When the CT value or average value of the region of interest exceeds the threshold, the pre-scan is stopped, and a preparation for a main-scan is started.

In X-ray computer tomography apparatuses, an ECG gated scan scheme of obtaining one or a series of images in a specific time phase by performing a scan in synchronism with an electrocardiographic wave is known. According to this scheme, in order to reduce motion artifacts due to the movement of the heart, the time (scan speed) required for the X-ray tube to rotate once is required to be sufficiently short compared with the cardiac cycle.

In order to maintain a high diagnostic value by reducing motion artifacts to a certain degree, a scan speed as short as, for example, 500 msec is required. It is not easy to realize a condition of a scan speed of 0.2 sec.

As a technique of reducing motion artifacts in a relatively popular apparatus whose scan speed is 1 or 0.5 sec, a technique called ECG gated reconstruction (segment scan) has been developed. In this segment scan, electrocardiogram data is acquired along with acquisition of projection data. On the basis of the electrocardiogram data, data (segment) in a partial period centered on a specific cardiac time phase is extracted from a projection data set in each cardiac cycle. A plurality of segments extracted from a plurality of cardiac cycles are joined to each other to prepare 360° projection data necessary for image reconstruction.

In a segment scan, the number of segments to be acquired is often set in advance. As the time width of a segment decreases, the number of segments required to be acquired increases, and the time resolution of an image increases. That is, the number of images in different cardiac time phases increases. In contrast to this, as the time width of a segment increases, the number of segments required to be acquired decreases, and the time resolution of an image decreases. If the number of segments acquired does not reach the predetermined number, an image with a predetermined time resolution cannot be obtained. In order to obtain an image with the predetermined time resolution, at least projection data corresponding to a heart rate corresponding to the predetermined number of segments to be acquired is required.

A segment scan is susceptible to the influences of motion artifacts. For this reason, this scan is performed while the patient holds his or her breath. There is a limit to the time during which the patient can hold his or her breath. In a segment scan, necessary projection data corresponding to the heart rate must be acquired within the limited breath holding period. In the segment scan, therefore, the heart rate of an object to be examined must be measured in advance, and the scan speed, i.e., the time required for the X-ray tube to rotate once, must be adjusted in accordance with the heart rate.

As described above, in bolus tracking method, a pre-scan is executed before a main-scan. When the segment scan scheme is applied to a main-scan, the time difference between the instant at which a scan speed is set and the instant at which a main-scan is started becomes long. Therefore, the heart rate in the main-scan may greatly change with respect to the heart rate at the time of setting the scan speed. For this reason, in some cases, the scan speed in a main-scan is not appropriate with respect to the actual heart rate. This problem becomes more noticeable in a contrast medium examination. This is because the heart rate often greatly changes due to the injection of a contrast medium.

BRIEF SUMMARY OF THE INVENTION

It is an object of the present invention to allow scan condition reset for a main-scan with respect to a change in physiological phenomenon of an object to be examined in a bolus tracking method by an X-ray computer tomography apparatus.

According to a first aspect of the present invention, there is provided an X-ray computer tomography apparatus which executes a pre-scan to acquire data for an object injected a contrast medium by using relatively low X-rays, and executes a main-scan to acquire data for the object by using relatively high X-rays after the pre-scan, comprising:

a determination unit configured to determine, on the basis of data of a physiological phenomenon of the object measured in a period between the start of injection of the contrast medium or the pre-scan and the end of the pre-scan, necessity of resetting a scan condition for the main-scan which is initially set on the basis of data of the physiological phenomenon of the object measured before injection of the contrast medium and a scan condition setting unit configured to reset, when the determination unit determines that it is necessary to reset the scan condition, the scan condition for the main-scan from the initially set scan condition to a scan condition corresponding to the data of the physiological phenomenon measured in the period between the start of injection of the contrast medium or the pre-scan and the end of the pre-scan.

According to a second aspect of the present invention, there is provided an X-ray computer tomography apparatus which executes a pre-scan to acquire data for an object injected a contrast medium by using relatively low X-rays, and executes a main-scan to acquire data for the object by using relatively high X-rays after the pre-scan, comprising a scan condition setting unit configured to set a scan condition for the main-scan on the basis of data of a physiological phenomenon of the object measured in a period between the start of injection of the contrast medium or the pre-scan and the end of the pre-scan.

According to a third aspect of the present invention, there is provided an X-ray computer tomography apparatus which executes a pre-scan to acquire data for an object injected a contrast medium by using relatively low X-rays, and executes a main-scan to acquire data for the object by using relatively high X-rays after the pre-scan, comprising a display unit configured to display the data of a physiological phenomenon of the object in time graph and numerical value and also display an input field concerning a scan condition for the main-scan, an input unit configured to input a scan condition for the main-scan in the input field, and a scan condition setting unit configured to set a scan condition for the main-scan in accordance with a scan condition input in a period between the start of the contrast medium or the pre-scan and the end of the pre-scan.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

DETAILED DESCRIPTION OF THE INVENTION

An X-ray computer tomography apparatus according to a preferred embodiment of the present invention will be described with reference to the several views of the accompanying drawing. Note that X-ray computer tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring, and only an X-ray tube rotates around an object to be examined. The present invention can be applied to either type. In this case, the rotate/rotate type, which is currently the mainstream, will be exemplified.

In addition, image reconstruction methods include a 360° method which requires 360° projection data corresponding to one rotation around an object to be examined and a half scan method which requires (180°+fan angle) projection data. The present invention can be applied to either of these methods. In this case, the 360° method will be exemplified.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified.

Recently, with advances toward the commercialization of a so-called multi-tube type X-ray CT apparatus having a plurality of pairs of X-ray tubes and X-ray detectors mounted on a rotating ring, related techniques have been developed. The present invention can be applied to both a conventional single-tube type X-ray CT apparatus and a multi-tube type X-ray CT apparatus. In this case, the single-tube type X-ray CT apparatus will be exemplified here.

Furthermore, an X-ray computer tomography apparatus uses a single-slice type X-ray detector with a single detection element array having a plurality of X-ray detection elements arrayed along the channel direction, or a multi-slice type X-ray detector having a plurality of detection element arrays juxtaposed in the slice direction. The present invention can use either of these types. In this case, the former type, i.e., the single-slice type X-ray detector, will be exemplified.

Figure 1:
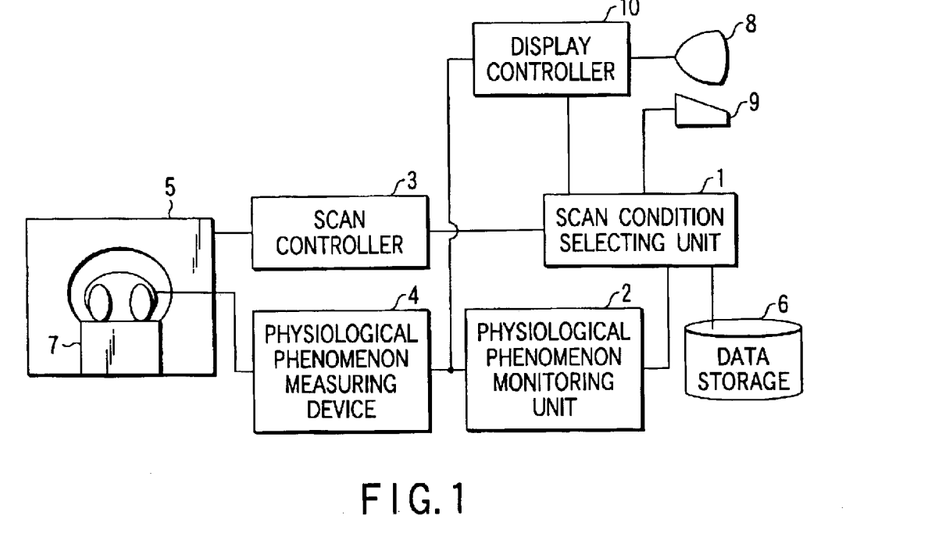
FIG. 1 is a block diagram showing the arrangement of the main part of an X-ray computer tomography apparatus according to an embodiment of the present invention.

FIG. 1 shows the arrangement of the main part of the X-ray computer tomography apparatus according to this embodiment. A gantry 5 houses the X-ray tube and X-ray detector. The X-ray tube is mounted, together with the X-ray detector, on a rotating frame having a ring-like shape. The X-ray tube faces the X-ray detector through an imaging space. An object to be examined which is placed on a couch 7 is placed in the imaging space of the gantry 5. The couch 7 moves in its longitudinal direction. In general, the body axis of the object is almost parallel to the longitudinal axis of the couch 7 and the rotation axis of the X-ray tube. A direction parallel to the rotation axis of the X-ray tube is called a slice direction. A high-voltage generating unit applies a tube voltage and supplies a filament current to the X-ray tube to generate X-rays. X-rays transmitted through the object generate electric charges in the respective X-ray detection elements. These electric charges are extracted as a current signal. This current signal is converted into a voltage signal by a data acquisition system (DAS). This signal is amplified and converted into a digital signal. The digital signal is stored as projection data, together with electrocardiogram data, in a storage through a slip ring and preprocessor. An image reconstructing unit reconstructs image data based on 360° projection data. The image reconstructing unit includes an ECG gated reconstruction function. According to the ECG gated reconstruction function, data (segment) within a partial period around a specific cardiac time phase is cut from a projection data set in each cardiac cycle on the basis of electrocardiogram data. A plurality of segments cut from a plurality of cardiac cycles are joined to each other, thereby preparing 360° projection data necessary for image reconstruction. Image data corresponding to a specific cardiac time phase is reconstructed on the basis of the prepared 360° projection data. The reconstructed image data is displayed on a display 8 through a display controller 10.

A physiological phenomenon measuring device 4 measures a physiological phenomenon of the object. The physiological phenomenon includes heartbeat (the movement of the heart), respiration, and the like. In this case, a physiological phenomenon will be described as "heartbeat". The electrocardiograph 4 detects an electrical phenomenon of the heart through an electrode attached to the object, and outputs electrocardiogram data representing a change in the electrical phenomenon over time. A physiological phenomenon monitoring unit 2 is connected to the electrocardiograph 4. The physiological phenomenon monitoring unit 2 calculates the number of heartbeats per minute, i.e., a heart rate, on the basis of the electrocardiogram data. The physiological phenomenon monitoring unit 2 also checks, on the basis of the calculated heart rate, whether a change in heart rate at the current time point with respect to the heart rate at a specific time point, i.e., the time point at which a heart rate was measured which was referred to when a main-scan condition was initially set exceeds a predetermined value. If the change in heart rate exceeds the predetermined value, the physiological phenomenon monitoring unit 2 outputs a signal prompting for main-scan condition reset, together with a signal representing the heart rate, to a scan condition selecting unit 1. That is, the physiological phenomenon monitoring unit 2 checks the necessity of resetting main-scan condition on the basis of the heart rate of the object. Note that a change in heart rate is calculated as the difference or the rate of change between the current heart rate and the heart rate which was referred to when a main-scan condition was initially set before injection of a contrast medium.

Upon reception of the signal prompting for scan condition reset from the physiological phenomenon monitoring unit 2, the scan condition selecting unit 1 determines optimal or approximately optimal scan conditions with respect to the heart rate received together with the signal. In practice, the scan condition selecting unit 1 selects scan conditions corresponding to the heart rate from a table written in advance in a storage medium such as a semiconductor memory, magnetic disk, or magnetooptical disk, which is possessed by a data storage 6.

Figure 2:
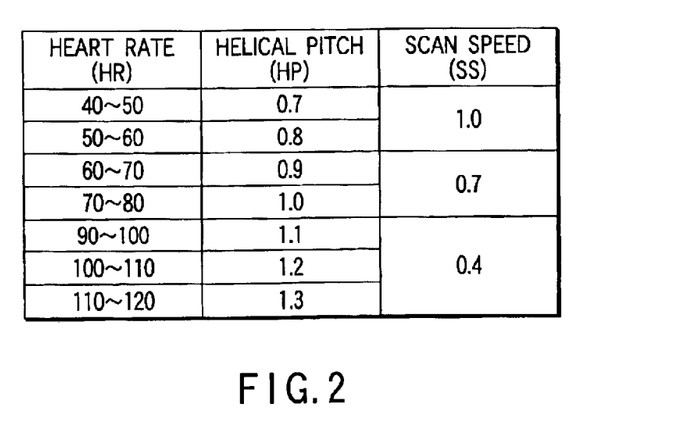
FIG. 2 is a view showing an example of a table (heart rate/helical pitch/scan speed) stored in a data storage in FIG. 1.

As shown in FIG. 2, for example, in this table, a plurality of sections concerning heart rates (HRs) are set, and a plurality of helical pitches (HPs) and scan speeds are associated with the sections. Referring to FIG. 2, in the table, different sections concerning heart rates (HRs) are set for different helical pitches and scan speeds. However, heart rates may be segmented within the same section. A helical pitch is a scan condition used in helical scan, and can be defined as the distance (mm) that the couch 7 moves while the X-ray tube rotates once. A scan speed can be defined as the time (sec) required for the X-ray tube to rotate once.

In the table, relatively high scan speeds are associated with relatively high heart rates, and vice versa. In addition, in the table, relatively long helical pitches are associated with relatively high heart rates, and vice versa. With such association, a main-scan condition can be so reset as to complete a main-scan (helical scan) in a predetermined scan range within a predetermined time, ensure the number of segments required in the ECG gated reconstruction method, and prevent an excessive decrease in time resolution.

Note that in addition to helical pitch and scan speed, scan conditions include a scan range, the maximum scan time during which the breath can be held (the upper limit of the scan time), the minimum necessary number of segments in the ECG gated reconstruction method, a specific cardiac time phase (a delay time from the R wave in an electrocardiogram), a tube voltage, a tube current, a slice width, and the like. Of these scan conditions, a helical pitch and scan speed are sensitive to a heart rate. If, for example, the heart beats slow and the heart rate decreases, the number of segments required for the ECG gated reconstruction cannot be prepared unless the scan speed is decreased or the helical pitch is decreased. On the other than, if the scan speed and helical pitch are excessively decreased, acquisition of predetermined projection data throughout the scan range cannot be completed within the upper limit of the scan time. On the contrary, when the heart beats fast and the heart rate increases, the number of segments required for ECG gated reconstruction can be prepared within a short scan time, even if the scan speed and helical pitch are increased. In addition, acquisition of projection data throughout the predetermined scan range can be completed. However, excessive increases in scan speed and helical pitch leave a room for improvement in time resolution. In the above table, helical pitches and scan speeds are properly determined with respect to heart rates so as to balance such a relationship.

Referring back to FIG. 1, the data of the main-scan condition selected by the scan condition selecting unit 1 is supplied to a scan controller 3. The scan controller 3 controls the rotational speed of the X-ray tube and the moving speed of the couch 7 in accordance with the supplied scan condition. For example, the scan controller 3 controls the rotating frame driving unit of the gantry 5 to make the rotating frame reach a set scan speed within a predetermined period of time and maintain the speed. The scan controller 3 then controls the high-voltage generating unit to start heating up the filament of the X-ray tube so as to reach a temperature corresponding to a tube current condition within a predetermined period of time. The scan controller 3 also controls the X-ray stop unit to adjust its opening in accordance with a slice thickness condition. The scan controller 3 further controls a couch driving unit to reach a speed corresponding to the helical pitch in a predetermined period of time, thereby starting moving the couch.

Figure 3:
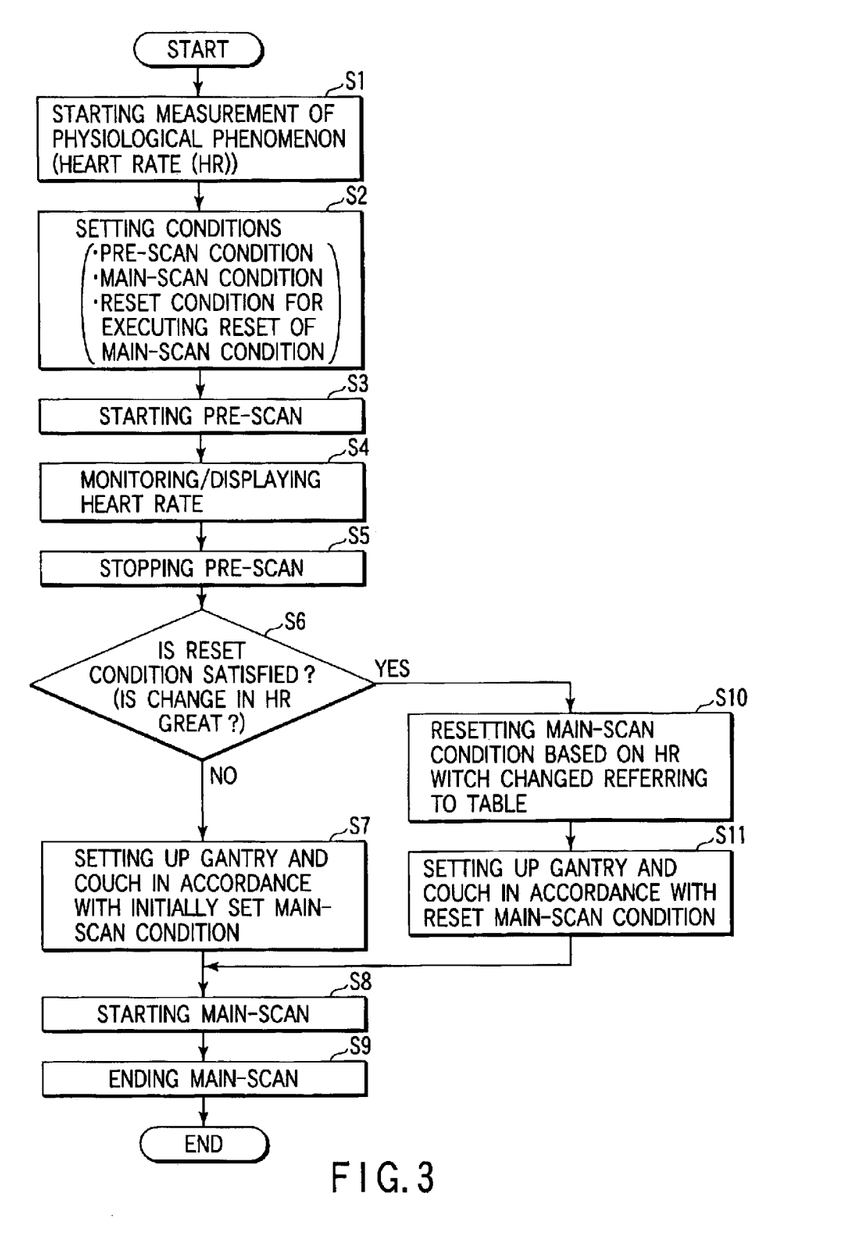
FIG. 3 is a flow chart showing a procedure for a bolus tracking method in this embodiment.
Figure 4:
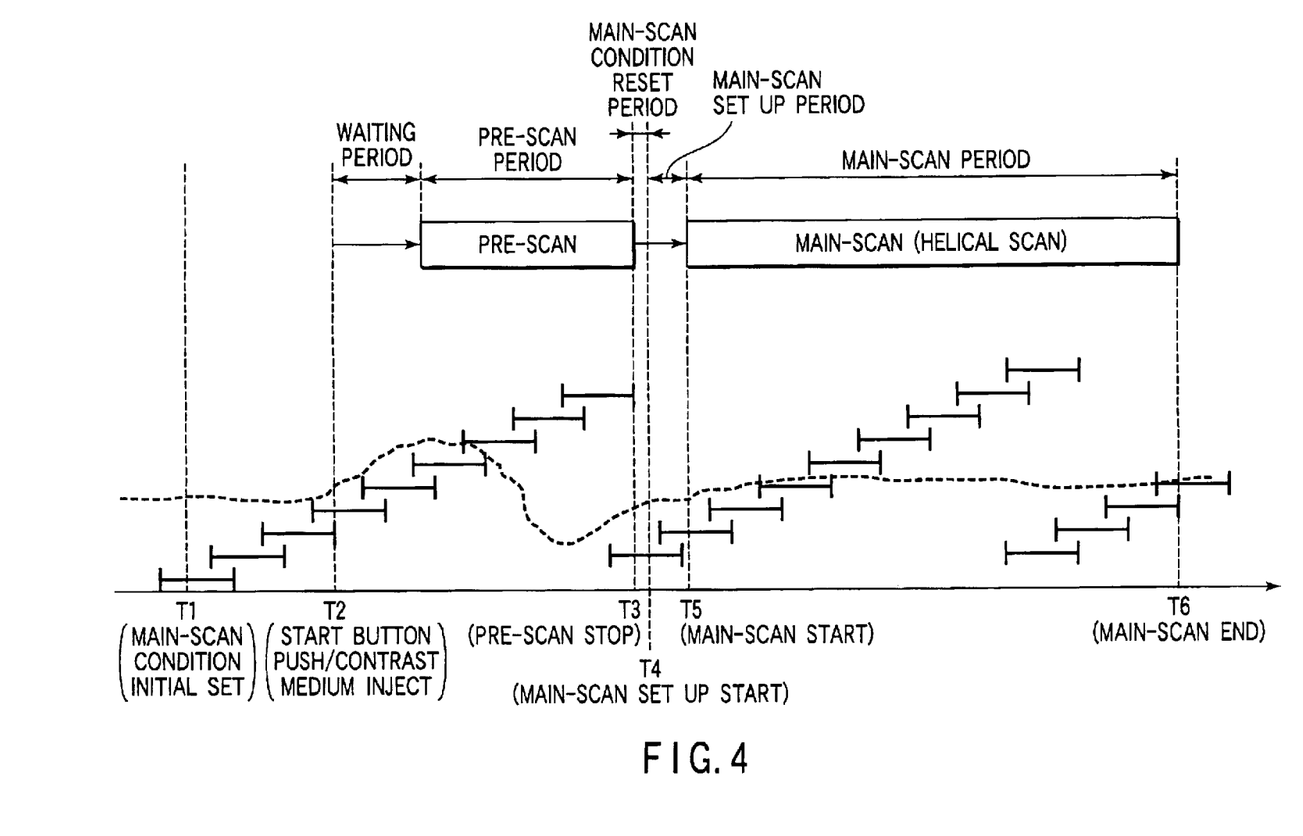
FIG. 4 is a timing chart of the bolus tracking method in FIG. 3.

FIG. 3 shows a procedure for a bolus tracking method in this embodiment. FIG. 4 is a timing chart of a bolus tracking operation. As preparatory operation for a bolus tracking operation, the physiological phenomenon measuring device 4 starts measuring an electrocardiogram (S1). This measurement is continued until a main-scan is completed after injection of a contrast medium and pre-scan are sequentially done.

In the pre-scan, projection data for the object is continuously acquired by using relatively low X-rays, and the CT values of pixels in the ROI or averaged CT value representing a density of the constract medium in the ROI is monitored. In the main-scan, projection data for the object is acquired by using relatively high X-rays after the pre-scan.

The electrocardiograph 4 calculates a heart rate on the basis of the measured electrocardiogram. A main-scan condition is set on the basis of the heart rate. In practice, however, the heart rate slightly varies. It is therefore preferable that heart rates be averaged in a predetermined time width, e.g., five sec immediately before the setting operation, or a median value within a predetermined time width be specified, and a main-scan condition be set on the basis of this average value or median value. For the sake of descriptive convenience, assume that a main-scan condition is set on the basis of a heart rate. The calculated heart rate is displayed, together with electrocardiogram data, on the display 8 through the display controller 10.

The operator operates an input operation unit 9 by referring to the displayed electrocardiogram and heart rate to input a pre-scan condition, a main-scan condition, and the reset condition for executing reset of the main-scan condition (S2). Note that specified values have almost been determined for many items of the pre-scan condition. That is, the following are set: a relatively low tube voltage and tube current which are set to suppress X-ray irradiation to a minimum, a thin slice width, a high scan speed to increase time resolution, and a small number of reconstruction matrices to improve immediacy. In addition, a pre-scan position, a contrast medium concentration monitoring region, a condition for a transition from a pre-scan to a main-scan (a threshold for a contrast medium concentration), and the like are manually set.

In addition, many items of a main-scan condition, e.g., a tube voltage, tube current, slice width, reconstruction matrix, and imaging field of view (FOV), are almost determined in accordance with an examination purpose, the sex and physique of an object, and the like. A scan range in which data acquisition is performed by a helical scan is set to, for example, a range covering the entire region of the heart. Furthermore, the upper limit of the time during which each patient can hold his or her breath is unique and the minimum necessary number of segments in the ECG gated reconstruction method are set. "Helical pitch (HP) and "scan speed" are set to values corresponding to the heart rate by the scan condition selecting unit 1 by referring to the table in the data storage 6. Alternatively, these items are manually input by the imaging technician.

The reset condition for executing reset of a main-scan condition represents a rule stating that an initially set main-scan condition should be reset to a main-scan condition corresponding to the heart rate at the end of a pre-scan when the heart rate immediately before a main-scan, the heart rate at the end of a pre-scan or a similar time in practice, changes from the heart rate at the time of initially setting a main-scan condition in the preparatory stage for the above bolus tracking method to a specific extent.

If, for example, the heart rate at the time of initial setting is "60" in the table shown in FIG. 2, this heart rate is included in the "60–70" section in the table. Therefore, the helical pitch HP "0.9" in this section is set. If, however, the heart rate measured at the end of a pre-scan falls outside the "60–70" section, a helical pitch HP corresponding to this heart rate should be set. On the other hand, the heart rate that has changed due to the injection of a contrast medium may restore its normal value with a lapse of time. That is, even if the heart rate greatly changes at the end of a pre-scan, it may tend to stabilize thereafter, and restores its normal value at the time of a main-scan. Obviously, in some cases, the heart rate may remain changed and does not restore its normal value. The heart rate changes differently among individuals. Therefore, a doctor or imaging technician should checks at the time of a main-scan whether the heart rate has restored to the normal value. This determination is reflected in a reset condition. The doctor or imaging technician can arbitrarily set whether to reset a main-scan condition when a section corresponding to the heart rate immediately before a main-scan shifts from a section corresponding to the heart rate at the time of initial setting by a specific number of steps.

Figure 7:
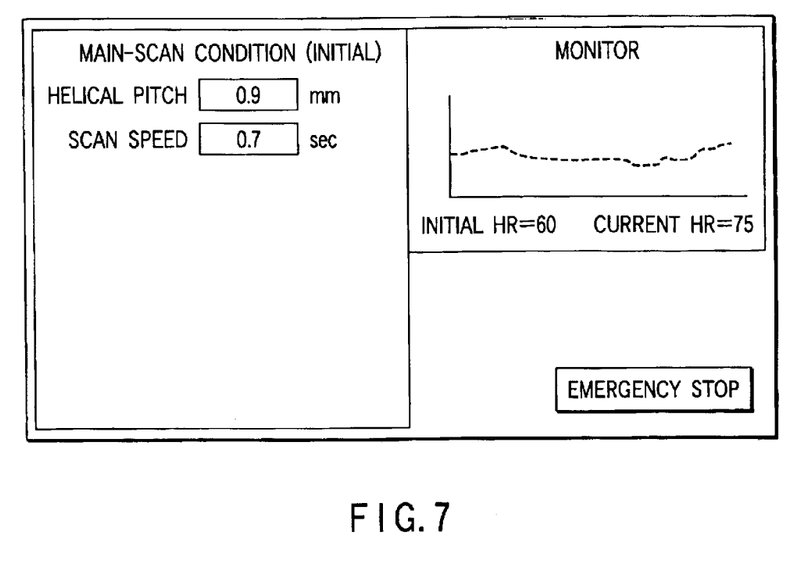
FIG. 7 is a view showing an example of a display window when an initially set main-scan condition is maintained in this embodiment.

When the start button of the input operation unit 9 is pressed at time T2 after the completion of the above initial setting, a contrast medium is automatically injected from an injector unit into the patient. A pre-scan is started after the time required for a contrast medium to reach a monitoring position since the injection of the contrast medium (S3). That is, a small dose of X-rays are continuously generated while the X-ray tube and X-ray detector continuously rotate around the object at high speed with respect to a positioned slice, thereby periodically acquiring data. Along with the pre-scan, the image reconstructing unit reconstructs image data from projection data in real time (S2). A CT value in a region of interest set in advance is extracted from the image data. This value or the average value of the CT values of a plurality of pixels in the region of interest is compared with a threshold for a shift to a main-scan. The CT values or the average value of the CT values represents a density of the contrast medium in the region of interest. The physiological phenomenon measuring device 4 continues measuring a heart rate during this pre-scan. As shown in FIG. 7, the heart rate is displayed in time graph and numerical value (S4).

As shown in FIG. 7, the heart rate which was referred to when scan conditions were initially set is displayed together with the current heart rate. The initially set scan speed and helical pitch are also displayed in numerical value. An emergency stop button is displayed together with these pieces of information. The heart rate of an object to be examined may abruptly change due the influences of the injection of a contrast medium and the like. In such a case, the imaging technician can perform emergency stop of a pre-scan and main-scan by clicking the emergency stop button.

When the CT value reaches the threshold for a shift to a main-scan or the imaging technician manually presses a main-scan shift trigger button (T3), the pre-scan is terminated (S5). The physiological phenomenon monitoring unit 2 checks whether a change in heart rate measured at the end of this pre-scan in a short period of time until time T4 satisfies a reset condition for executing reset of a main-scan condition (S6). That is, the difference between the heart rate which was referred to when the pre-scan condition was initially set and the heart rate measured at the end of the pre-scan is compared with the threshold for the reset condition.

Figure 5:
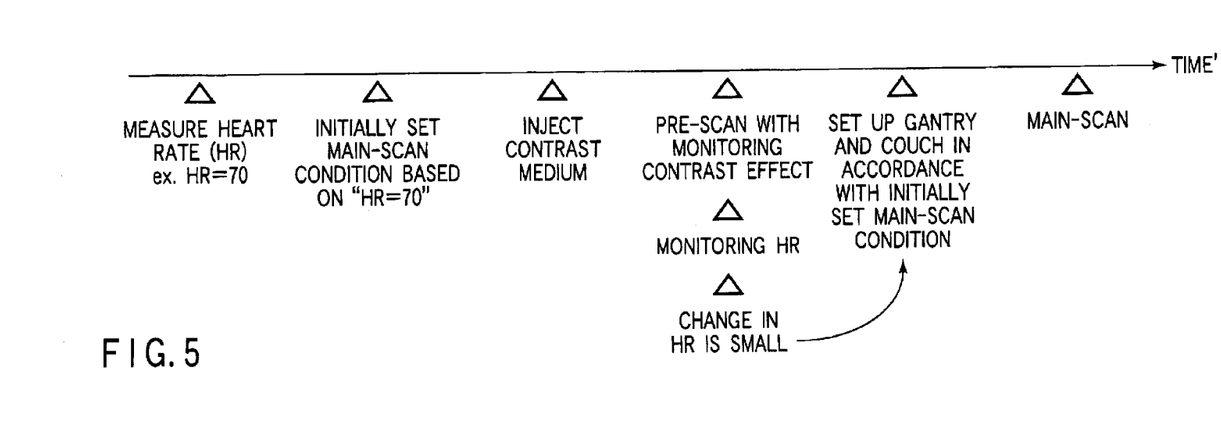
FIG. 5 is a view for supplementarily explaining steps S6 and S7 in FIG. 3.

If the absolute value of this difference has not reached the threshold for the reset condition, it is determined that the change in heart rate is relatively small enough so as not to satisfy the reset condition, and the physiological phenomenon monitoring unit 2 sends no signal for prompting for resetting a main-scan condition to the scan condition selecting unit 1. With this operation, as shown in FIG. 5, the scan condition selecting unit 1 sends the initially set main-scan condition to the scan controller 3 or instructs the scan controller 3 to start a setup under the initially set main-scan condition. The scan controller 3 then starts a setup for a main-scan at time T4 under the sent initially set main-scan condition (S7). The scan controller 3 completes the setup until time T5, and starts a main-scan at time T5 (S8). The scan controller 3 terminates the main-scan at time T6 when data are completely acquired from the entire scan range (S9).

Figure 6:
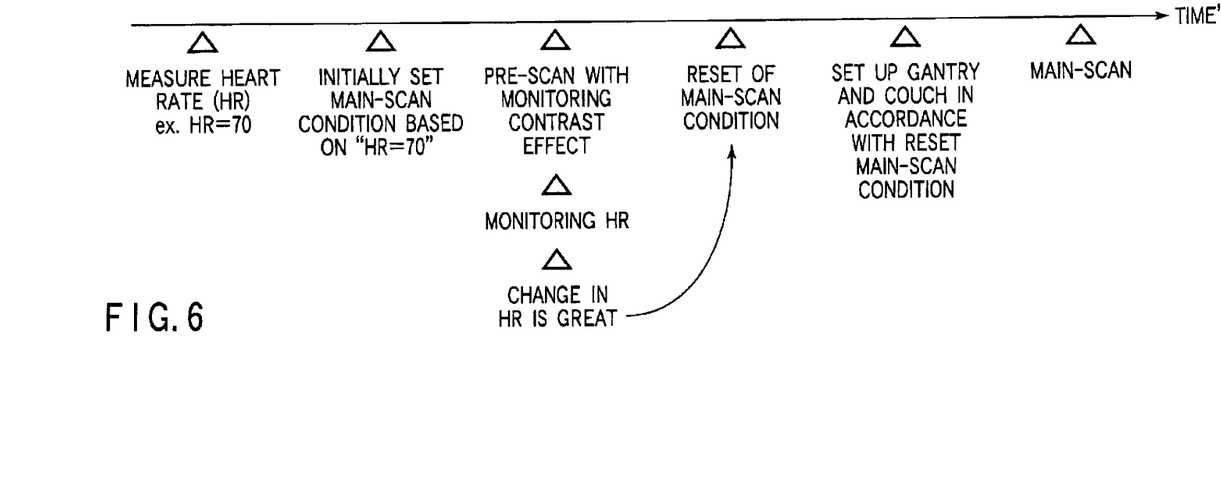
FIG. 6 is a view for supplementarily explaining steps S6, S10, and S11 in FIG. 3.

If it is determined in step S6 that the absolute value of the difference between the heart rate which was referred to when a scan condition was initially set and the heart rate at the end of the pre-scan has reached the threshold of a reset condition, it is determined that a change in heart rate is relatively large enough to satisfy the reset condition. The physiological phenomenon monitoring unit 2 then sends a signal prompting for resetting a main-scan condition, together with the heart rate measured at the end of the pre-scan, to the scan condition selecting unit 1. With this operation, as shown in FIG. 6, the scan condition selecting unit 1 selects a helical pitch and scan speed corresponding to the heart rate at the end of the pre-scan by referring to the table in the data storage 6, and resets the main-scan condition from the initially set helical pitch and scan speed to the selected helical pitch and scan speed (S10).

Figure 8:
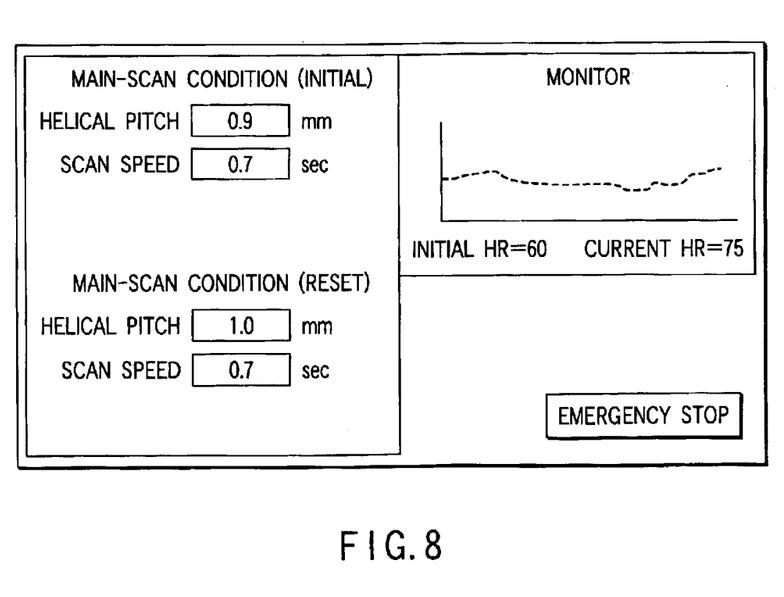
FIG. 8 is a view showing an example of a display window when a main-scan condition is reset in this embodiment.

When the helical pitch and scan speed are reset, the display controller 10 displays the reset helical pitch and scan speed, together with the initially set helical pitch and scan speed, as shown in FIG. 8. The imaging technician can recognize whether a helical pitch and scan speed are reset depending on whether the reset helical pitch and scan speed are displayed.

In performing an ECG gated scan, the scan condition selecting unit 1 recalculates a "delay time" from the R wave to a specific time phase by multiplying the cardiac cycle (the reciprocal of the heart rate) at the end of the pre-scan by the ratio of the time width from the R wave to the specific time phase to the cardiac cycle at the time of setting a time phase of interest (specific time phase).

According to the above description, the necessity of resetting a main-scan condition is determined on the basis of the difference between the heart rate at the time of initially setting a main-scan condition and the heart rate at the end of a pre-scan, and a main-scan condition is reset on the basis of the heart rate at the end of the pre-scan. However, the present invention is not limited to the heart rate at the end of a pre-scan, and the necessity of resetting an initially set scan condition may be determined on the basis of a heart rate measured at any given time point from the start of injection of a contrast medium or a pre-scan to the end of the pre-scan. In addition, a main-scan condition may be reset on the basis of the heart rate measured at any given time point in this period. The necessity of resetting a main-scan condition is determined on the basis of the heart rate at the end of a pre-scan, i.e., the time point nearest to the start of a main-scan. In addition, by resetting a main-scan condition, the main-scan condition can be approximated to the optimal main-scan condition corresponding to the actual heart rate at the time of execution of a main-scan. Alternatively, the necessity of resetting the initially set scan condition may be determined on the basis of the heart rate measured at any given time point in this period, and a main-scan condition is reset. Even in this case, the main-scan condition can be approximated more to the above optimal value than when a main-scan is executed under the main-scan condition initially set before the injection of a contrast medium.

The scan condition selecting unit 1 sends the reset main-scan condition to the scan controller 3. With this operation, the scan controller 3 sets up the gantry 5 and couch 7 in accordance with the reset main-scan condition (S11). After the completion of the setup, a main-scan is executed with X-ray irradiation (S8, S9).

As described above, when the heart rate changes, a main-scan condition, and more specifically a helical pitch and scan speed, is reset to solve the problem that, for example, the number of segments required for an ECG gated reconstruction cannot be completely prepared, and acquisition of projection data throughout a planned scan range within the upper limit of a scan time. In addition, this can improve the time resolution.

Figure 9:
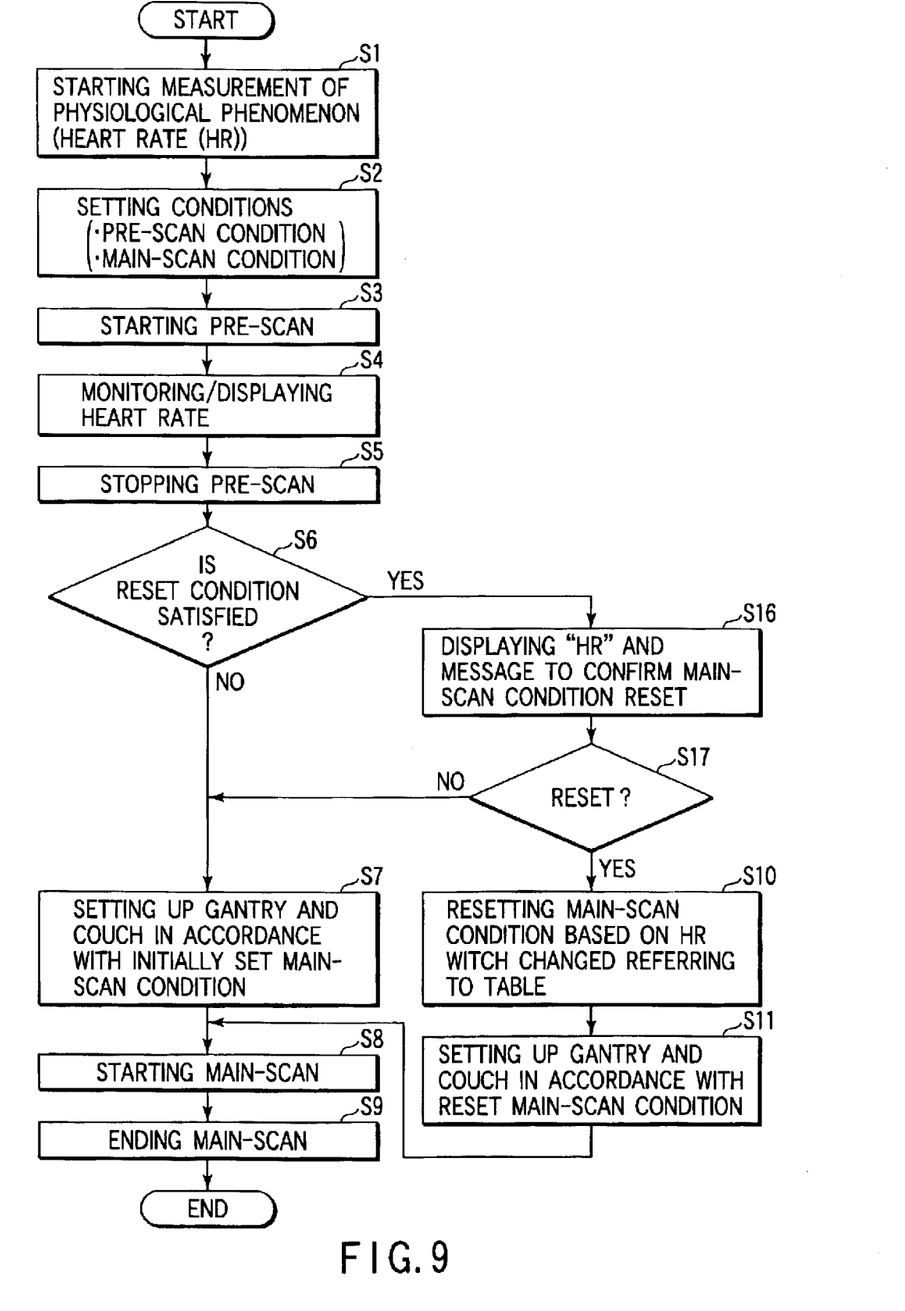
FIG. 9 is a flow chart showing a procedure for a bolus tracking method according to the first modification of this embodiment.

If it is determined in step S6 in FIG. 9 that a change in heart rate is relatively large enough to satisfy the reset condition, the display controller 10 may cause the display 8 to display, together with this heart rate, a message to confirm main-scan condition reset and the reset continue/stop button, thereby finally confirming the necessity of main scan reset operation (S16). If it is instructed to do no reset (S17), setup of the gantry 5 and couch 7 is started in accordance with the main-scan condition initially set in step S7, and a main-scan is performed under the condition (S8, S9). If it is instructed to do reset (S17), a main-scan condition is reset in step S10, and the gantry 5 and couch 7 are set up in accordance with the condition (S11).

Since the operator is made to finally determine the necessity of reset at the end of a pre-scan, an adverse effect of resetting of a main-scan condition can be avoided even at the occurrence of a negligibly small event of changing the heart rate temporarily in a very short period of time near the end of a pre-scan.

Figure 10:
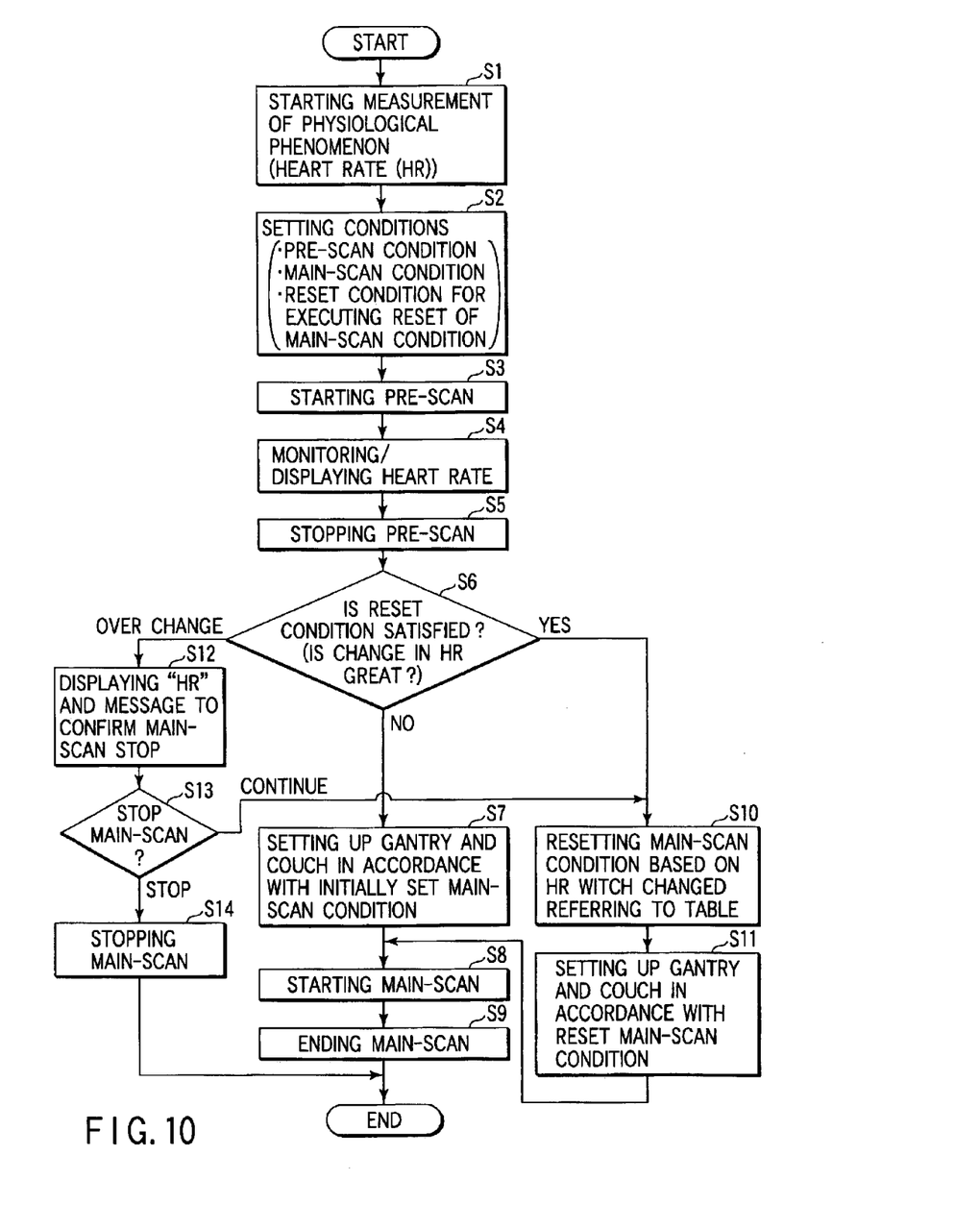
FIG. 10 is a flow chart showing a procedure for a bolus tracking method according to the second modification of this embodiment.

If the heart rate excessively changes, i.e., a very peculiar situation occurs in which the heart rate greatly changes by, for example, three or five steps on the table, the main-scan is preferably stopped in some case. In order to cope with such a situation, when the physiological phenomenon monitoring unit 2 determines that the heart rate has changed by a predetermined number of steps, e.g., three or five steps, on the table, the scan condition selecting unit 1 may cause the display 8 to display a message to confirm main-scan stop and the main scan continue/stop button, together with the heart rate that has greatly changed (S12). If the operator (imaging technician) instructs to continue the main-scan (S13), the main-scan is executed under the main-scan condition reset through steps S10 and S11 in accordance with the heart rate that has greatly changed. If the operator instructs to stop the main-scan (S13), emergency stop of a shift to the main-scan is performed by a system controller or interlocking circuit (not shown) in step S14.

Figure 11:
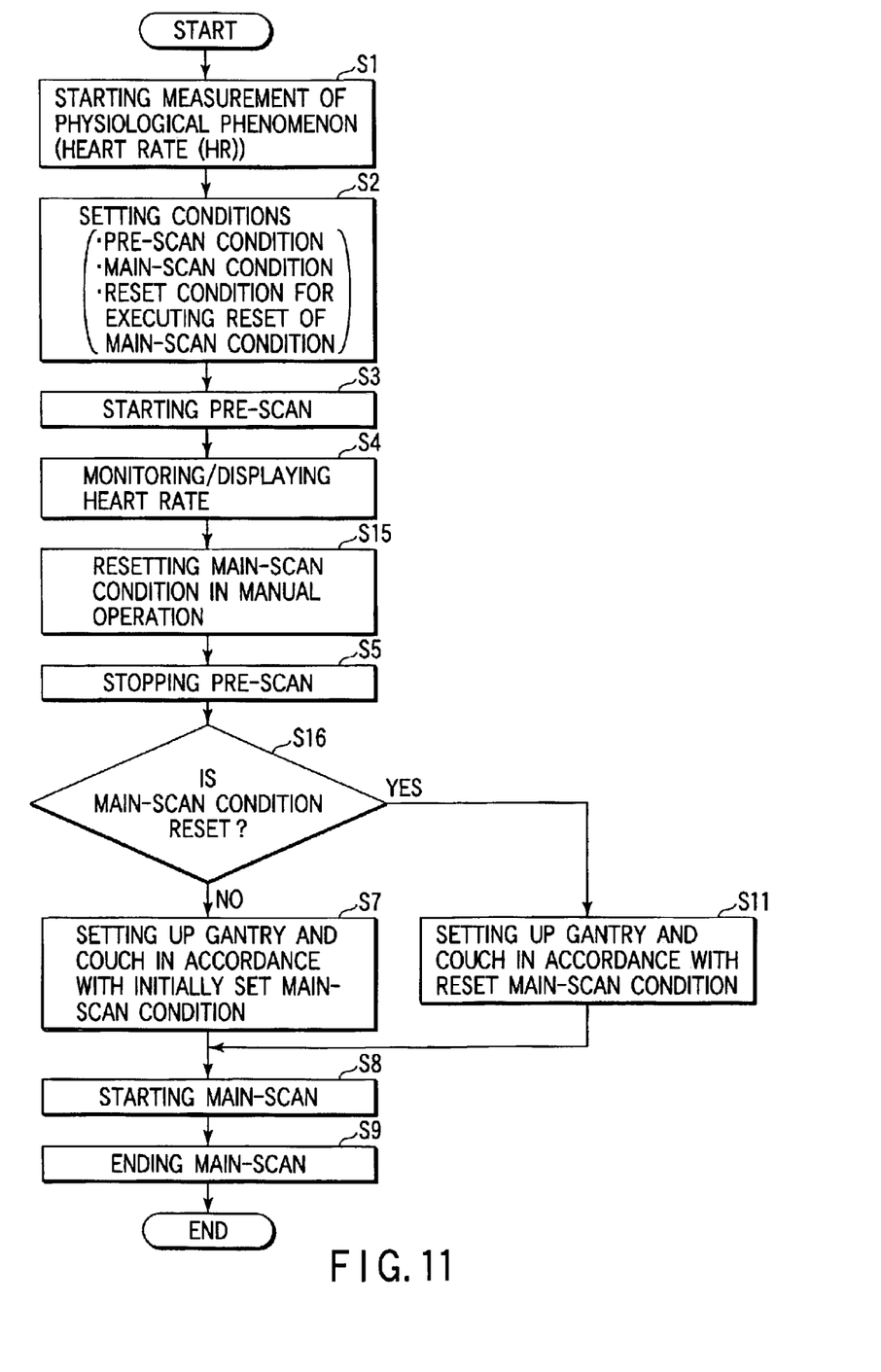
FIG. 11 is a flow chart showing a procedure for a bolus tracking method according to the third modification of this embodiment.
Figure 12:
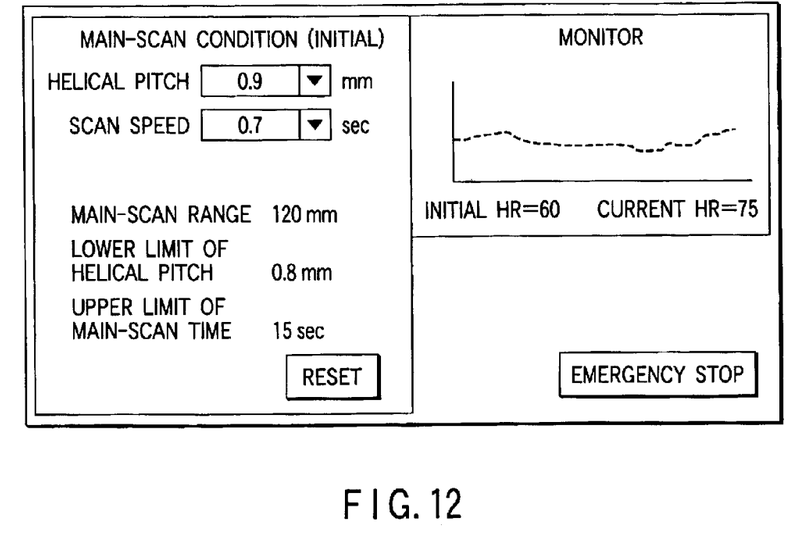
FIG. 12 is a view showing an example of a display window in the third modification of this embodiment.

Alternatively, a main-scan condition may be manually reset as shown in FIG. 11. As shown in FIG. 12, the display controller 10 displays a measured heart rate in time graph and numerical value and input fields associated with a main-scan condition. In the input fields, the initially set helical pitch and scan speed are displayed, and a plurality of helical pitch candidates and a plurality of scan speed candidates are displayed on pulldown menus adjacent to the respective fields. In addition, a scan range, the lower limit of a helical pitch which satisfies the condition that a main-scan can be completed in a predetermined scan range within a predetermined period of time, and the maximum period of time during which an object can hold its breath, i.e., the upper limit of a main-scan time, are displayed. The imaging technician operates the input operation unit 9 to select a helical pitch and scan speed from the respective candidates by referring to the scan range, the lower limit of the helical pitch, and the upper limit of the main-scan time, together with the heart rate, thereby resetting a helical pitch and scan speed (S15). If a main-scan cannot be completed in the predetermined scan range within the predetermined period of time under the condition of the selected helical pitch and scan speed, or the necessary number of segments cannot be prepared, the display controller 10 determines this, and rejects the reset of the scan condition input upon this selection. The display controller 10 also displays, on the display 8, a message to prompt for reselection of a helical pitch and scan speed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus which executes a pre-scan to acquire data for an object injected a contrast medium by using relatively low X-rays, and executes a main-scan to acquire data for the object by using relatively high X-rays after the pre-scan, comprising:
 a determination unit configured to determine, on the basis of data of a physiological phenomenon of the object measured in a period between the start of injection of the contrast medium or the pre-scan and the end of the pre-scan, necessity of resetting a scan condition for the main-scan which is initially set on the basis of data of the physiological phenomenon of the object measured before injection of the contrast medium; and
 a scan condition setting unit configured to reset, when the determination unit determines that it is necessary to reset the scan condition, the scan condition for the main-scan from the initially set scan condition to a scan condition corresponding to the data of the physiological phenomenon measured in the period between the start of injection of the contrast medium or the pre-scan and the end of the pre-scan.

2. An apparatus according to claim 1, wherein the scan condition setting unit maintains the initially set scan condition when the determination unit determines that it is not necessary to reset the scan condition.

3. An apparatus according to claim 1, wherein the scan condition setting unit resets the scan condition on the basis of data of the physiological phenomenon measured at the end of the pre-scan.

4. An apparatus according to claim 1, wherein the scan condition setting unit comprises a storage configured to store a table in which a plurality of scan conditions are associated with a plurality of steps concerning the physiological phenomenon.

5. An apparatus according to claim 1, wherein the determination unit determines necessity of resetting the scan condition on the basis of a degree of a change in physiological phenomenon measured in the period between the start of injection of the contrast medium or the pre-scan and the end of the pre-scan with respect to the physiological phenomenon of the object measured before the injection of the contrast medium.

6. An apparatus according to claim 1, wherein the physiological phenomenon measuring device measures a heart rate of the object.

7. An apparatus according to claim 1, wherein the determination unit determines necessity of resetting the scan condition on the basis of the data of the physiological phenomenon measured at the end of the pre-scan.

8. An apparatus according to claim 7, wherein the scan condition setting unit resets the scan condition on the basis of the data of the physiological phenomenon measured at the end of the pre-scan.

9. An apparatus according to claim 6, wherein the determination unit determines necessity of resetting the scan condition on the basis of an average value or median value of heart rates within a predetermined time width.

10. An apparatus according to claim 9, wherein the determination unit resets the scan condition on the basis of the average value or median value of heart rates.

11. An apparatus according to claim 1, further comprising a display unit which displays the data of the measured physiological phenomenon in time graph or numerical value in real time.

12. An apparatus according to claim 11, wherein the display unit displays information indicating whether the scan condition is reset, together with the data of the physiological phenomenon.

13. An apparatus according to claim 11, wherein the display unit displays data of a physiological phenomenon which was referred to initially set the scan condition, together with the real-time data of the physiological phenomenon.

14. An apparatus according to claim 11, wherein the display unit displays a button for performing emergency stop of the pre-scan and the main-scan, together with the data of the physiological phenomenon.

15. An apparatus according to claim 1, wherein the scan condition setting unit resets the scan condition on a precondition that the main-scan is completed in a predetermined scan range within a predetermined period of time.

16. An X-ray computer tomography apparatus which executes a pre-scan to acquire data for an object injected a contrast medium by using relatively low X-rays, and executes a main-scan to acquire data for the object by using relatively high X-rays after the pre-scan, comprising a scan condition setting unit configured to set a scan condition for the main-scan on the basis of data of a physiological phenomenon of the object measured in a period between the start of injection of the contrast medium or the pre-scan and the end of the pre-scan.

17. An X-ray computer tomography apparatus which executes a pre-scan to acquire data for an object injected a contrast medium by using relatively low X-rays, and executes a main-scan to acquire data for the object by using relatively high X-rays after the pre-scan, comprising:

a display unit configured to display the data of a physiological phenomenon of the object in time graph and numerical value and also display an input field concerning a scan condition for the main-scan;

an input unit configured to input a scan condition for the main-scan in the input field; and a scan condition setting unit configured to set a scan condition for the main-scan in accordance with a scan condition input in a period between the start of the contrast medium or the pre-scan and the end of the pre-scan.

18. An apparatus according to claim 17, wherein the scan condition setting unit sets a scan condition for the main-scan in accordance with a scan condition input last in a period between the start of inject of the contrast medium or the pre-scan and the end of the pre-scan.

19. An apparatus according to claim 17, wherein the scan condition setting unit has a function of rejecting setting of the input scan condition when the main-scan cannot be completed in a predetermined scan range within a predetermined period of time under the input scan condition.

20. An apparatus according to claim 17, wherein the display unit displays a candidate of the scan condition which allows the main-scan to be completed in a predetermined scan range within a predetermined time period.

* * * * *